US00PP26547P3

(12) United States Plant Patent
Werner

(10) Patent No.: US PP26,547 P3
(45) Date of Patent: Mar. 29, 2016

(54) ***BUDDLEJA* PLANT NAMED 'PINK MICRO CHIP'**

(50) Latin Name: ***Buddleja* hybrid**
Varietal Denomination: Pink Micro Chip

(71) Applicant: North Carolina State University, Raleigh, NC (US)

(72) Inventor: Dennis James Werner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 133 days.

(21) Appl. No.: 13/999,799

(22) Filed: Mar. 21, 2014

(65) Prior Publication Data

US 2015/0052651 P1 Feb. 19, 2015

(30) Foreign Application Priority Data

Aug. 19, 2013 (CA) ..... PBR 13-8096

(51) Int. Cl.
*A01H 5/02* (2006.01)

(52) U.S. Cl.
USPC ..... Plt./242
CPC ..... *A01H 5/02* (2013.01)

(58) Field of Classification Search
USPC ..... Plt./242
See application file for complete search history.

(56) References Cited

PUBLICATIONS

Flowering Shrubs, Spring Meadow Nursery, Inc. Starter Plants Catalog and Shrub Reference 2013-2014; Aug. 25, 2013, pp. 11; ('Blue Chip Jr.' *Buddleia*).

*Primary Examiner* — June Hwu
(74) *Attorney, Agent, or Firm* — Myers Bigel & Sibley, P.A.

(57) ABSTRACT

*Buddleja* 'Pink Micro Chip' is a new and distinct variety of butterfly bush that has the following unique combination of desirable features that are outstanding in a new variety. 'Pink Micro Chip' has low vigor resulting in very dwarf stature. 'Pink Micro Chip' is asexually propagated using softwood or semi-hardwood cuttings. 'Pink Micro Chip' demonstrates a dense, spreading growth habit. 'Pink Micro Chip' is lacking male flower parts (anthers), resulting in male (pollen) sterility. 'Pink Micro Chip' produces female structures that are essentially sterile, resulting in lack of seed formation. 'Pink Micro Chip' has red-purple flower color.

4 Drawing Sheets

Latin name of the genus and species: Genus: *Buddleja*. Species: hybrid.

Variety denomination: The inventive cultivar of *Buddleja* disclosed herein has been given the variety denomination 'Pink Micro Chip'.

RELATED APPLICATION INFORMATION

This application claims priority under 35 U.S. §119(a) to Canadian Plant Breeder's Rights Application No. 13-8096, filed Aug. 19, 2013; the disclosure of which is incorporated herein by reference in its entirety.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventor in Raleigh, N.C., United States. One of the objectives of the breeding program was to develop a dwarf statured, male and female sterile, spreading *Buddleja* with red-purple (RHS 72C) flowers. 'Pink Micro Chip' was selected at a research station in Jackson Springs, N.C. in 2010 from a population of about 150 seedling progeny derived from a hand pollinated cross of 'Lilac Chip' (U.S. Plant Pat. No. 24,016)×'Miss Molly' made in summer 2009 in Raleigh, N.C. 'Lilac Chip' was the female (seed) parent, and 'Miss Molly' was the male (pollen) parent in the aforementioned hybridization. 'Lilac Chip' is a complex hybrid containing 3 different species and one botanical variety of *Buddleja* (*B. davidii, B. davidii* var. *nanhoensis, B. lindleyana*, and *B. globosa*). 'Miss Molly' was derived from hybridization of 'Miss Ruby'×'Attraction'. 'Miss Ruby' was derived from hybridization of 'White Ball'× 'Attraction'. 'White Ball' is a complex hybrid, presumably containing *B. davidii* and *B. fallowiana*. 'Attraction' was derived as an open-pollinated seedling of 'Honeycomb', which is a hybrid of *B. globosa*×*B. davidii*. NC2000-1 is a hybrid of 'Nanho Purple'×*Buddleja lindleyana*. 'Nanho Purple' is a variety derived from *Buddleja davidii* var. *nanhoensis*. All of the hybridizations described above, with the exception of the development of 'White Ball' and 'Attraction', were accomplished in the inventor's research program. The complete pedigree of 'Pink Micro Chip' is shown in FIG. 4. Of all the parents used in the development of 'Pink Micro Chip', the varieties 'Blue Chip' (U.S. Plant Pat. No. 19,991), 'Miss Molly' (U.S. Plant Pat. No. 23,425), 'Miss Ruby' (U.S. Plant Pat. No. 19,950), 'Attraction' (not patented), 'White Ball' (not patented), 'Nanho Purple' (not patented), and 'Honeycomb' (not patented), and the species *Buddleja lindleyana* are available in commerce.

The seeds resulting from the 2009 controlled hybridization process were harvested in fall of 2009 and germinated in a greenhouse in Raleigh, N.C. in the winter of 2010. The resulting 150 seedlings (approximate) were planted in field trials in spring of 2010 at a research station in Jackson Springs, N.C. These plants flowered in summer 2010, and one plant, designated NC2010-22, was selected in July, 2010 for its very dwarf stature, spreading habit, attractive red-purple (RHS 72C) colored flowers, oblong-elliptic leaves, flowers lacking anthers (male sterile), and lack of seed set (female sterile). This original plant demonstrated characteristics identical to those subsequently expressed on other plants when propagated from stem cuttings. This single plant is the subject of the present invention *Buddleja* 'Pink Micro Chip'.

The inventor conducted the first asexual propagation of 'Pink Micro Chip' in fall 2010 in Raleigh, N.C., and 'Pink Micro Chip' has subsequently been propagated in the same location in years 2011 through 2013. In all cases, the original plant selection was propagated asexually by softwood to semi-hardwood stem cuttings. Such cuttings root readily under mist in about 14 to 21 days, and resume normal growth. Four plants derived from stem cuttings of the variety were established in experimental greenhouse trials in Raleigh, N.C. in fall, 2010 and in 2011. Subsequently, ten plants derived from stem cuttings were established in a field trial in Jackson Springs, N.C. in 2013. Through successive asexual propagations, the characteristics of the original plant have been maintained. Thus, plants derived from stem cuttings exhibit characteristics identical to those of the original plant, and no aberrant phenotypes have appeared.

Test plantings and performance evaluation over four years at a research station in Jackson Springs, N.C. and a greenhouse in Raleigh, N.C. demonstrate this variety to be relatively consistent in its characteristics even under the different growing conditions associated with yearly climatic variation.

Plants of the new variety are very dwarf after establishment in the field, being less vigorous and more dwarf than most cultivars of butterfly bush available in commerce. Young plants have averaged about 38 cm of height growth per year. Plants are spreading in growth habit. Flowering occurs in the first year of growth on newly formed wood. The inflorescence is a panicle, and shows a light red-purple flower color. Flowering usually begins in late May to early June in Jackson Springs, N.C., and continues throughout the growing season until the first freeze event in October or November. An individual inflorescence flowers for about 7-10 days, depending on temperature, but new flowers are made during the entire growing season. Flowers are essentially female sterile, and the new cultivar has set no seed to date in greenhouse or field trials, even under conditions of intentional controlled pollination, an asset in landscape plantings.

'Pink Micro Chip' is distinguished from other related known cultivars based on the unique combination of traits including very dwarf plant size, dense spreading growth habit, green leaves (RHS 137C) with oblong-elliptic shape, attractive red-purple (RHS 72C) flower color, lack of anthers (male sterility), and female structures that are essentially sterile. "Essentially sterile" is used because applicant does not preclude the possibility that seed set may be observed on rare occasions. The cultural requirements for 'Pink Micro Chip' are well-drained soil, full sun, and moderate moisture. 'Pink Micro Chip' exhibits no serious pest or disease problems known to the inventors, except for occasional spider mite infestation during periods of hot, dry weather.

SUMMARY OF THE INVENTION

'Pink Micro Chip' is a new and distinct variety of butterfly bush that has the following unique combination of desirable features outstanding in a new variety. In combination these traits set 'Pink Micro Chip' apart from all other existing varieties of butterfly bush known to the inventors.

1. 'Pink Micro Chip' has low vigor resulting in very dwarf stature.
2. 'Pink Micro Chip' is asexually propagated using softwood or semi-hardwood cuttings.
3. 'Pink Micro Chip' demonstrates a dense, spreading growth habit.
4. 'Pink Micro Chip' exhibits absence of anthers (male sterility).
5. 'Pink Micro Chip' has female structures that are essentially sterile (female sterility).
6. 'Pink Micro Chip' has light red-purple (RHS 72C) flower color.
7. 'Pink Micro Chip' has oblong-elliptic leaf shape.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'Pink Micro Chip'. Photographs were taken from one-year-old plants growing in Jackson Springs, N.C.

DETAILED BOTANICAL DESCRIPTION OF THE VARIETY

The following is a detailed description of the botanical and ornamental characteristics of the subject butterfly bush 'Pink Micro Chip'. Color data are based on *The Royal Horticultural Society Colour Chart*, The Royal Horticultural Society, London, 2007 edition. Where dimensions, sizes, colors and other characteristics are given, it is to be understood that such characteristics are approximations of averages set forth as accurately as practicable.

The descriptions reported herein are from one-year-old specimens grown in field research trials in Jackson Springs, N.C.

Genus: *Buddleja.*

Species: Complex hybrid, including davidii, globosa, and lindleyana.

Denomination: 'Pink Micro Chip'.

Commercial classification: Shrub, deciduous.

Common name: Butterfly bush.

Type: Ornamental.

Uses: Patio container plant, herbaceous perennial border, or shrub border for residential and commercial landscapes.

Cultural requirements: Full sun exposure, well-drained soil, and moderate moisture.

Figure 1:
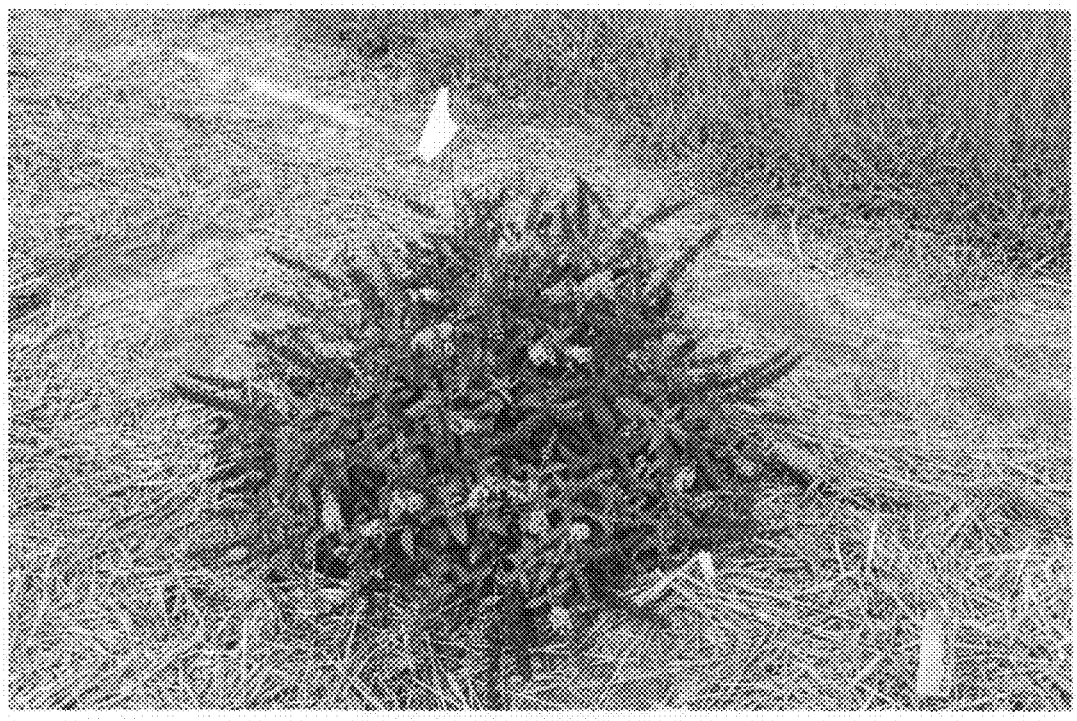
FIG. 1 shows a typical plant of 'Pink Micro Chip', showing the dwarf stature, spreading growth habit, dense foliage, and red-purple flowers.
Figure 2:
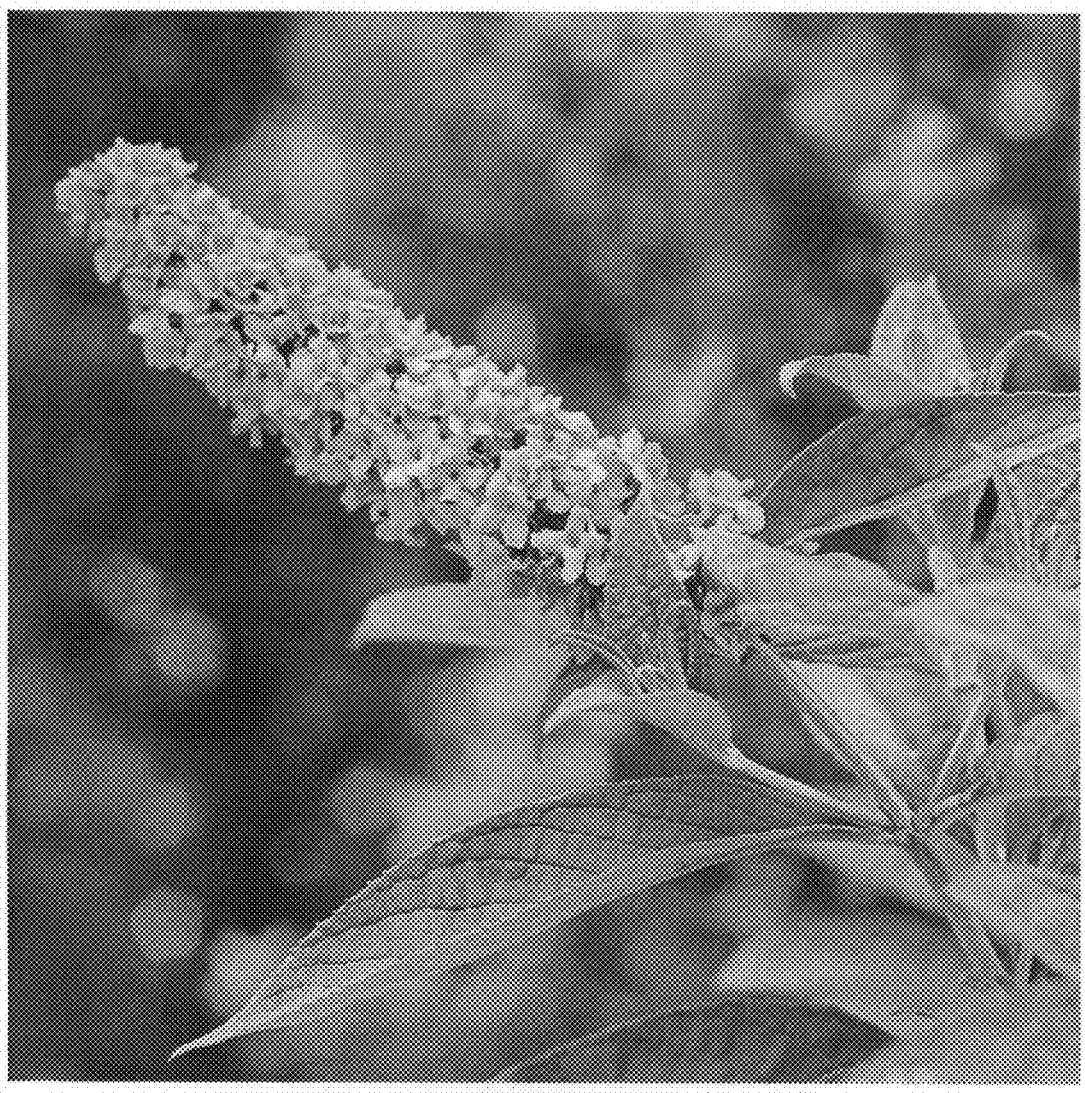
FIG. 2 shows the entire inflorescence of 'Pink Micro Chip'.
Figure 3:
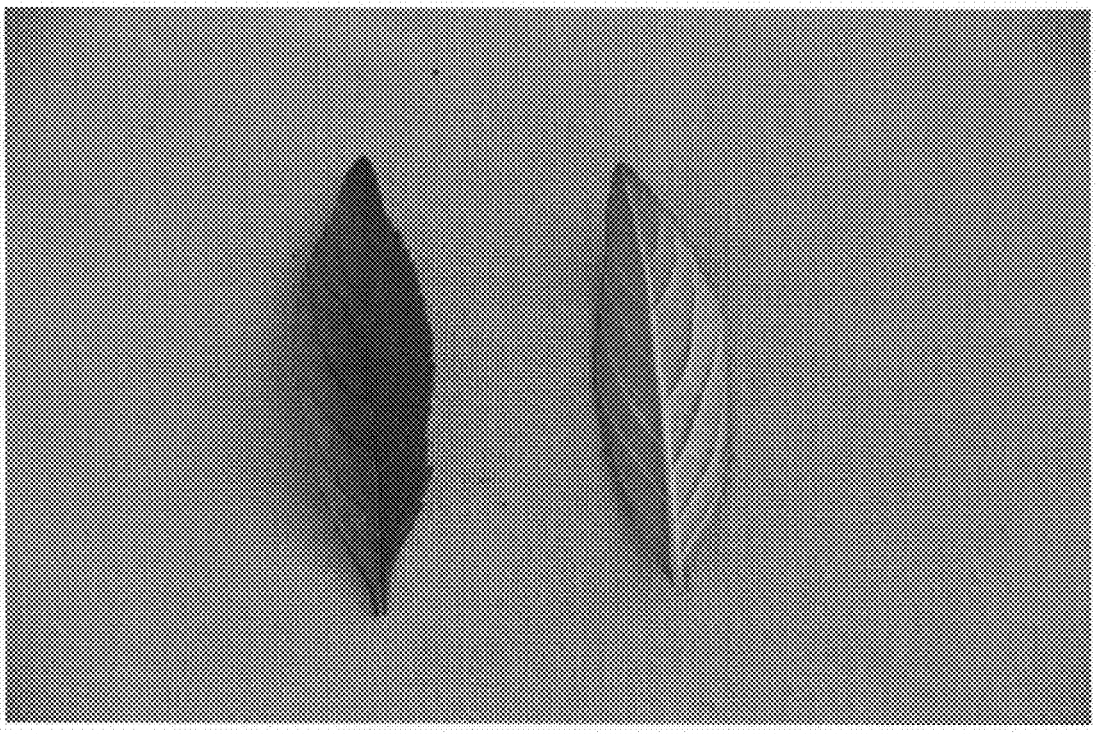
FIG. 3 shows the typical coloration and form of leaves of 'Pink Micro Chip'. This figure shows the upper (top) and lower (bottom) leaf surface.
Figure 4:
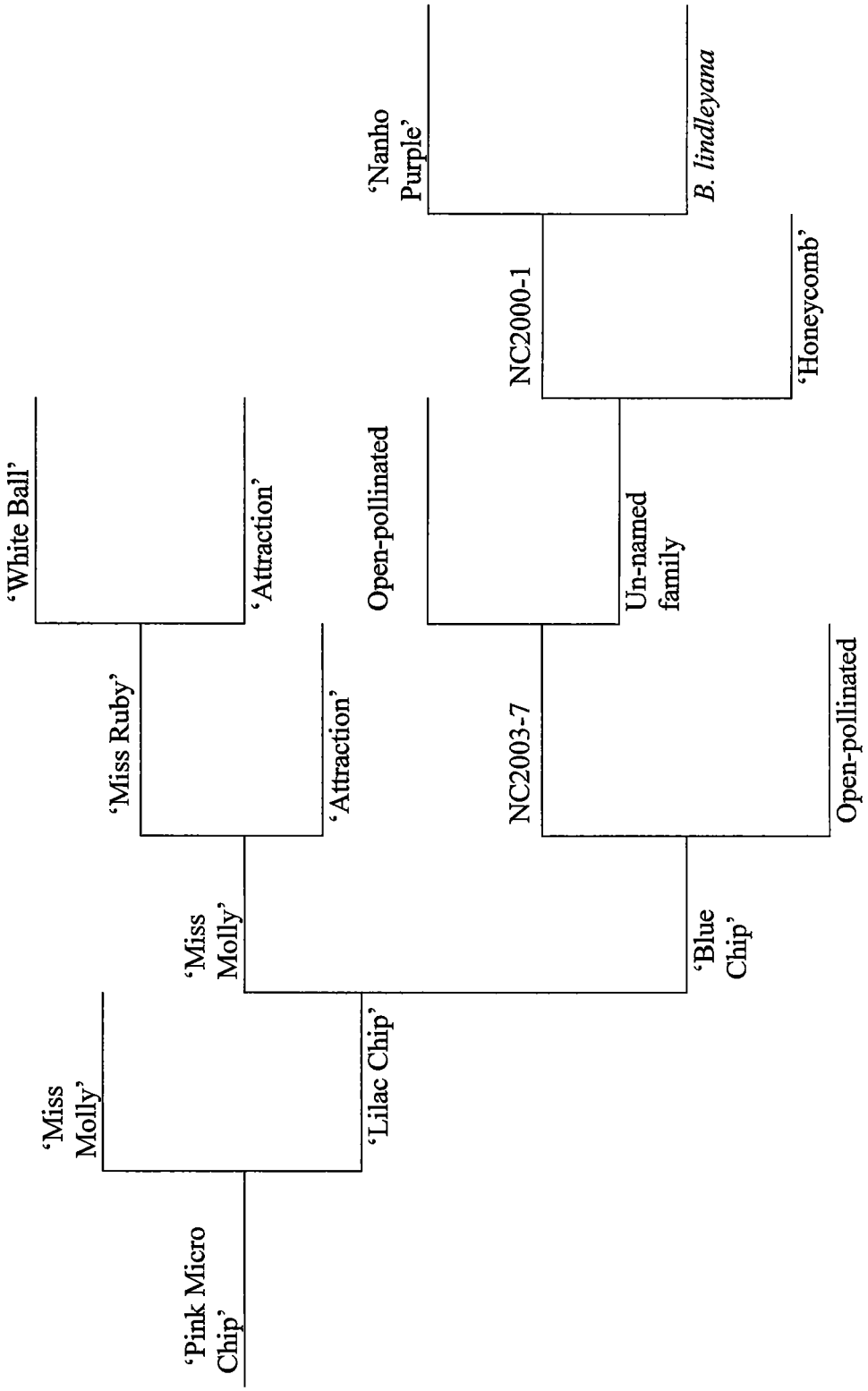
FIG. 4 shows the complete pedigree of 'Pink Micro Chip'.

Parentage: 'Pink Micro Chip' is a sixth-generation hybrid that resulted from the most recent cross pollination of 'Lilac Chip'×'Miss Molly'. See FIG. 4 for the entire pedigree.

Plant description:

*Blooming period*.—June through October.
*Blooming habit*.—Paniculate.
*Vigor*.—Low vigor.
*Plant habit*.—Dwarf, spreading habit.
*Height and spread*.—0.38 m (height) and 0.77 m (width) on one-year-old unpruned plants.
*Hardiness*.—To date, hardy to minus 14 degrees Centigrade (7 degrees Fahrenheit). Not tested below this temperature. Anticipated adapted to USDA hardiness zones 5-9.
*Propagation*.—Softwood to semi-hardwood cuttings under intermittent mist. Roots typically form in 2-3 weeks.
*Root system*.—Fibrous, spreading.
*Seasonal interest*.—Red-purple (RHS 72C) flowers in spring, summer, and fall on a very dwarf shrub with spreading growth habit.
*Disease and pest susceptibility and resistance*.—No particular susceptibility or resistance, except occasionally susceptible to spider mites under very hot and dry conditions.
*Special growing requirements*.—Moderate yearly pruning in late winter or early spring prior to bud break is recommended to encourage more profuse flowering.

Stems:

*Shape*.—Stem cross section is quadrangular.
*Length*.—Average 38 cm in one year of growth.
*Color*.—Yellow-green (RHS 145B) on recently formed shoots.
*Diameter*.—3 mm at base of new growth.
*Stem surface*.—Slight pubescence.
*Pubescence*.—Sparse.
*Internode length*.—3.4 cm in the middle of new growth.

Foliage:

*Type*.—Deciduous.
*Leaf arrangement*.—Opposite, decussate.
*Leaf division*.—Simple.
*Leaf shape*.—Oblong-elliptic.
*Leaf base*.—Attenuate.
*Leaf apex*.—Acute.
*Leaf venation*.—Pinnate.
*Leaf surface* (*abaxial*).—Slightly pubescent.
*Leaf margin*.—Serrulate.
*Leaf attachment*.—Petiolate.
*Petiole dimensions*.—2.4 mm length. 1 mm width.
*Petiole shape*.—Sulcate and slightly pubescent.
*Petiole color*.—Yellow-green (RHS 146C).
*Leaf color*.—Adaxial side=green (RHS 137C). Abaxial side=grayed-green (RHS 191C).
*Leaf midrib color*.—Abaxial side=greyed-green (RHS 194C).
*Leaf length*.—Average length=5.0 cm.
*Leaf width*.—Average width=1.9 cm.
*Foliar fragrance*.—None detectable.

Flowers:

*Inflorescence*.—Dense panicle, terminal and axillary.
*Inflorescence shape*.—Cylindrical.
*Flower shape*.—Salverform.
*Petals*.—4 in number.
*Fused or unfused*.—Fused at base.
*Petal margin*.—Entire.
*Petal apex*.—Rounded lobes, serrulate.
*Petal base*.—Truncate.
*Petal surfaces*.—Lacking pubescence.
*Petal shape*.—Rotund.
*Petal dimensions*.—7.4 mm total length. 5.6 mm width at apex. 1 mm width at base.
*Petal color*.—Adaxial and abaxial surface (open flower) =Red-purple (RHS 72C). Closed flower prior to opening=Red-purple (RHS 72A).
*Corolla tube color*.—Outside of corolla=Red-purple (RHS 72C).
*Corolla throat color*.—Inside of corolla=Yellow-orange (RHS 21D).
*Corolla tube surfaces* (*inner and outer surfaces*).—Pubescence lacking.
*Corolla tube shape*.—Tubular.
*Corolla lobe arrangement*.—Touching to slightly overlapping.
*Corolla lobe attitude*.—Semi-erect.
*Color of peduncle*.—Green (RHS 142B).
*Peduncle surface*.—Glaucous.
*Peduncle length*.—15.6 cm.
*Peduncle shape*.—Flattened oval in cross section.
*Pedicel dimensions*.—1.9 mm in length and less than 1 mm in diameter.
*Pedicel color*.—Green (RHS 142B).
*Pedicel shape*.—Flattened oval in cross section.
*Pedicel surface*.—Glaucous.
*Flowers persistent or self-cleaning*.—Flowers are persistent.
*Lastingness of the overall inflorescence*.—7-10 days.
*Lastingness of an individual flower*.—3-5 days.
*Dimensions of inflorescence*.—15.6 cm length. 1.5 cm width at base, tapering to 0.5 cm at tip.
*Quantity of flowers*.—About 334 flowers per panicle (average number of panicles sampled was 5).
*Bud apex*.—Rounded lobes, serrulate.
*Bud surface*.—Glaucous. Lacking pubescence.
*Bud shape*.—Elongated, linear balloon.
*Calyx shape*.—Tubular.
*Calyx dimensions*.—1 mm in width and 2.6 mm in length.
*Sepals*.—Four in number.
*Sepal shape*.—Lanceolate.
*Sepal apex*.—Acute.
*Sepal margin*.—Entire.
*Sepal surface*.—Glabrous.
*Sepal color*.—Green (RHS 138B).
*Flower fragrance*.—Distinct sweet fragrance.

Reproductive organs:

*Stamens*.—Absent.
*Anther shape*.—Absent.
*Filament size*.—Absent.
*Pollen amount*.—Absent.
*Pistil*.—One in number.
*Pistil dimensions*.—3 mm in length, and less than 1 mm in diameter.
*Stigma color*.—Yellow-green (RHS 144C).
*Style color*.—Yellow-green (RHS 144D).
*Ovary*.—Present.
*Ovary position*.—Superior.
*Ovary shape*.—Oval.

*Fertility*.—Essentially male (pollen) and female (seed) sterile.

Fruit:

*Type*.—Absent. Essentially female sterile.

*Dimensions*.—Absent.

*Color*.—Absent.

Comparison with known cultivars. The closest comparisons known to the inventor are the varieties 'Blue Chip' (U.S. Plant Pat. No. 19,991), 'Ice Chip' (U.S. Plant Pat. No. 24,015), 'Lilac Chip' (U.S. Plant Pat. No. 24,016), and 'White Ball' (non-patented). Plants and flowers of this new variety differ from 'Blue Chip'. In direct comparisons of 'Pink Micro Chip' and 'Blue Chip' in the inventor's experimental trials, plants of 'Pink Micro Chip' show red-purple (RHS 72C) flower color, compared to the violet-blue (RHS 90C) flower color of 'Blue Chip'. 'Pink Micro Chip' also possesses longer panicles (inflorescences) than 'Blue Chip'. 'Pink Micro Chip', showing red-purple flower color, is distinctly different in flower color from 'Ice Chip' (white flower color, RHS NN155B), 'White Ball' (white flower color), and 'Lilac Chip' (violet flower color, RHS 84C). 'Pink Micro Chip' differs from its parent 'Miss Molly' in having much shorter stature. 'Miss Molly' has red-purple flower color (RHS 61B), compared to the lighter red-violet of 'Pink Micro Chip'. 'Pink Micro Chip' is male sterile (produces no anthers) and is essentially female sterile, compared to the high male and female fertility of 'Miss Molly'.

Herbarium Voucher:

A voucher of 'Pink Micro Chip' will be deposited into the Herbarium of North Carolina State University (NCSU) in Raleigh, N.C., USA upon patenting.

That which is claimed is:

1. A new and distinct variety of butterfly bush (*Buddleja*) plant named 'Pink Micro Chip' substantially as illustrated and described, characterized by its dwarf stature, dense and spreading growth habit, oblong-elliptic leaf shape, red-purple flower color, lack of male flower parts (anthers) resulting in male sterility, and female structures that are essentially sterile, resulting in no seed formation.

* * * * *